United States Patent
Ono

(10) Patent No.: US 7,291,135 B2
(45) Date of Patent: Nov. 6, 2007

(54) WINGED ANGLED NEEDLE ASSEMBLY

(75) Inventor: Seiichi Ono, Oita (JP)

(73) Assignee: Kawasumi Laboratories, Inc., Tokyo (JP)

( * ) Notice: Subject to any disclaimer, the term of this patent is extended or adjusted under 35 U.S.C. 154(b) by 0 days.

(21) Appl. No.: 11/206,097

(22) Filed: Aug. 18, 2005

(65) Prior Publication Data

US 2006/0047252 A1    Mar. 2, 2006

(30) Foreign Application Priority Data

Aug. 26, 2004   (JP)   ............................. 2004-246994

(51) Int. Cl.
   *A61M 5/00*   (2006.01)
(52) U.S. Cl. .................................... 604/263
(58) Field of Classification Search ................ 604/263, 604/264, 110, 187, 272
   See application file for complete search history.

(56) References Cited

U.S. PATENT DOCUMENTS

| | | | | |
|---|---|---|---|---|
| 4,631,058 | A * | 12/1986 | Raines | 604/263 |
| 6,537,255 | B1 * | 3/2003 | Raines | 604/177 |
| 6,824,530 | B2 * | 11/2004 | Wagner et al. | 604/162 |
| 6,997,902 | B2 * | 2/2006 | Thorne et al. | 604/110 |
| 2002/0111581 | A1 * | 8/2002 | Sasso | 604/93.01 |
| 2006/0047252 | A1 | 3/2006 | Ono | |

OTHER PUBLICATIONS

U.S. Appl. No. 11/391,320, filed Mar. 29, 2006, Ono et al.

* cited by examiner

*Primary Examiner*—Nicholas D. Lucchesi
*Assistant Examiner*—Melissa A McCorkle
(74) *Attorney, Agent, or Firm*—Oblon, Spivak, McClelland, Maier & Neustadt, P.C.

(57) ABSTRACT

A winged angled needle assembly has a hub to which a proximal end portion of an angled needle having a sharpened tip portion is joined and a pair of wings attached to both sides of the hub and further includes a fixing member attached so as to support the wings and an extensible, contractible needle guard disposed between the hub and the fixing member so as to connect these two members. The guard extends in the direction from the proximal end portion to the sharpened tip portion of the angled needle when extended, so that the tip portion can be encased in said guard simultaneously with pulling the angled needle out of an implanted port. The guard has an exposure prevention mechanism attached thereto and is externally stopped, so that the sharpened tip portion is kept from exposing once it is encased in the guard. The angled needle can have a length as required regardless of the length of the wings. The fixing member supports the wings opened to be coplanar with each other, serves to stably fix the winged angled needle assembly to an implanted port in an installed state and also works as a support for pulling the angled needle out of the port, so that the winged angled needle assembly can minimize the mental stress of a patient.

11 Claims, 4 Drawing Sheets

WINGED ANGLED NEEDLE ASSEMBLY

BACKGROUND OF THE INVENTION

1. Field of the Invention

The present invention relates to a winged angled needle assembly for constituting a port access infusion set, called PAIS) to be used for blood dialysis, fluid infusion, blood infusion, etc., and it relates particularly to a winged angled needle assembly improved in the form of a protective portion.

For effecting blood dialysis, blood filtering, blood infusion, fluid infusion or the delivery of a therapeutic fluid such as an anticancer medication, insulin, or the like into a vascular system for a long period of time, there has been developed an advanced method in which an implanted port (subcutaneous implanted part) is provided under the surface of the skin of a patient and an angled needle is caused to subcutaneously pierce the implanted port, in place of a conventional direct subcutaneous delivery of the blood system of a patient. PAIS is a device for use in a method using the above implanted port. The winged angled needle assembly is the needle suitably used in the PAIS and has a configuration in which the portion of the needle including a forward end portion to pierce the implanted port, is angularly disposed at approximately 90 degrees relative to a proximal end portion which is formed to join the support in the needle assembly.

In recent years, with the prevalence of infectious diseases that are taken on through such medical needles tainted with carriers' blood or body fluid, such as viral hepatitis, AIDS, etc., it is a very important task in medical facilities to prevent such infections caused by accidental needle-sticks to medical practitioners working on blood infusion, blood dialysis, etc., and environmental pollutions caused by disposal of infected needles.

With blood-stained needles, etc., to which blood is adhering, have very fine sizes, it is not always possible to prevent entirely accidental needle-sticks, wherein, a needle pierces the finger or hand of a medical practitioner whose finger(s) may come close to a needle end due to a subtle mistake in visual observation, even if he or she is considerably careful. From this point of view, it is strongly demanded that the winged angled needle assembly should be so structured to have mechanism or means for preventing accidental needle-sticks or protecting practitioners from accidental needle-sticks.

2. Description of the Related Art

U.S. Pat. No. 5,951,522 to Rosato et al discloses a hypodermic needle having mounted thereon a wing assembly which can take the form of a single integral member having a plurality of spaced apart fold lines which permits the integral member to be folded between a mounting position and a protective position or a pair of wing members which are mounted in a scissors arrangement which is movable between a mounting position and a protective position.

In the invention of Rosato et al, when the hypodermic needle is in an installed position (in a state where the angled needle is caused to pierce the port and a therapeutic fluid such as an anticancer medication or the like is infused), the wing assembly is folded perpendicular to the angled needle that is angled at 90 degrees relative to the hub. Further, when it is in a protective position (in a state where the angled needle is caused to pierce the port or it is pulled out of the port and discarded after infusion of the therapeutic fluid), the wing assembly extends in parallel with the angled needle and the angled needle is in a state where it is encased in the wing assembly.

However, the winged angled needle assembly (hypodermic needle) of Rosato et al still has some problems to solve. That is, (1) the size of the above wing assembly limits the usable length of the angled needle in the invention of Rosato et al. When the length of the angled needle is so limited, the application of the winged angled needle assembly to various patients is no longer possible since the depth of the subcutaneously implanted port differs among patients, so that its therapeutic application is limited. (2) When the angled needle of Rosato et al is pulled out of the implanted port after its use, a practitioner grabs (closes) the wing assembly with his or her index or middle finger and thumb, thereby to pull the angled needle out of the port and prevent accidental needle-sticks at the same time. However, when the above angled needle is inserted very tightly into the implanted port with no space between the needle and the port (for example, when the angled needle is inserted with pressure so tightly as the circumferential surface of the angled needle presses and outwardly open the cross-sectional portions of the wall of the port laterally), considerable power is required to pull the angled needle out of the port. However, it is difficult to grab and properly operate the above wing assembly with the index or middle finger and thumb of only one hand. This situation involves a problem that when a medical practitioner takes more time, handling the winged angled needle assembly, the more pain a patient is inflicted.

U.S. Pat. No. 6,500,155 to Sasso discloses a winged angled needle assembly comprising an angled needle and a pair of wing members mounted to side portions of the angled needle, in which channels for confining the distal end portion of the angled needle are formed in the wing members and the wing members are folded together towards the distal end portion of the angled needle to confine the distal end portion of the needle.

However, the winged angled needle assembly of Sasso has a problem that the accidental needle-sticks cannot be prevented simultaneously with pulling the angled needle out of the implanted port. In the state of the art with respect to recent winged angled needle assemblies, it is required to provide means capable of preventing accidental needle-sticks simultaneously in the process of pulling out the angled needle out of the implanted port. In U.S. Pat. No. 6,500,155 to Sasso, however, nothing is disclosed with regard to any effective means that can satisfy the above requirement for preventing accidental needle-sticks.

U.S. Pat. No. 5,584,813 to Livingston et al discloses a subcutaneous injection set (winged angled needle assembly) for subcutaneous placement of a distal end of a soft flexible cannula formed of a polytetrafluoroethylene tube, or the like, said injection set comprising a longitudinally collapsible injector and an insertion needle formed of a metal and having an eye formed therein for threaded reception of said distal end of said cannula.

In the winged angled needle assembly of Livingston et al, however, it is the soft flexible cannula that is inserted into the implanted port, and this cannula is inserted into the port, together with the insertion needle formed of a metal. That is, the cannula is inserted into, and implanted in, the port in a manner in which a thread (cannula) is passed through the eye of a needle (needle formed of a metal), and then, the needle formed of a metal is withdrawn and discarded in a state wherein the needle is encased in the collapsible injector.

(1) In the winged angled needle assembly of Livingston et al, however, the use of the insertion needle formed of a metal is essential, so that there is a risk of the cannula being damaged to form a pinhole when the cannula is inserted into the implanted port together with the needle formed of a metal. Further, it is difficult to insert the cannula smoothly into the implanted port by sliding the cannula through the hollow portion of the needle formed of a metal.

(2) When the cannula is formed of a PTFE tube, the cannula is easily kinked when made extremely curved, and the kinking may impair the infusion of therapeutic fluid. Further, there is another problem that the cannula formed of a flexible PTFE tube may be decreased in internal diameter due to a repulsive pressure exerted by the insertion portion (septum, or the like) of the implanted port formed from an elastomeric material such as a silicone rubber, or the like, which may impair or block the smooth infusion of therapeutic fluid.

(3) Further, when the collapsible injector unintentionally collapses while a practitioner is at work, the tip of the needle formed of a metal placed in the collapsible injector may become exposed accidentally and dangerously since the injector has no stopper to prevent it.

SUMMARY OF THE INVENTION

It is an object of the present invention to provide a winged angled needle assembly that can overcome the above various problems of conventional winged angled needle assemblies, for example, the problems that the therapeutic application is often restricted, since the length of a angled needle is determined and limited by the size of wing portions, thereby handling of a winged angled needle assembly is made difficult, that is, when a needle is tightly forced into an implanted port, the infusion of a therapeutic fluid is impaired if a flexible angled needle such as the cannula becomes kinked when extremely curved. And the infusion of a therapeutic fluid is liable to be blocked, since the cannula is often decreased in internal diameter, due to a repulsive pressure exerted by the implanted port formed from an elastomeric material such as a silicone rubber, or the like.

According to the present invention, there is provided the following winged angled needle assemblies.

(1) According to the present invention, there is provided a winged angled needle assembly 1 comprising a hub 3 to which a proximal end portion 2" of an angled needle 2 having a sharpened tip portion 2' is joined and a pair of wings 4 attached to both sides of said hub 3, the winged angled needle assembly 1 further comprising a fixing member 5 attached so as to support said wings and an extendable, contractible needle guard 6 disposed between said hub 3 and said fixing member 5 so as to connect these two members, wherein said guard 6 thereby extends in the direction from said proximal end portion 2" of said angled needle 2 to said sharpened tip portion 2' when extended, so that said tip portion 2' can be encased in said guard 6.

(2) According to the present invention, there is also provided a winged angled needle assembly as recited in (1), wherein said fixing member 5 has an insertion hole 9 through which said angled needle is to be inserted, the insertion hole being formed nearly in the center of said fixing member, the winged angled needle assembly 1 having a constitution in which the angled needle 2 can be inserted through said insertion hole 9 when said winged angled needle assembly 1 is used, and said angled needle 2 can be pulled out in a manner in which the proximal end portion 2" first passes through the insertion hole and then the sharpened tip portion 2' passes through the insertion hole.

(3) According to the present invention, further, there is provided a winged angled needle assembly as recited in (1) or (2), wherein said guard 6 has, attached thereto, stop members 8 or engagement members 11 and 12 as a means for preventing the exposure of the angled needle 2.

(4) According to the present invention, further, there is provided a winged angled needle assembly as recited in (3), wherein a stop plate or stop hook is attached as said stop members 8 to said guard 6 to be opposed with each other and a concave portion or groove and a convex portion or projection are attached as said engagement members 11 and 12 to said guard 6 to be opposed with each other.

(5) According to the present invention, further, there is provided a winged angled needle assembly as recited in (1) or (2), wherein a tubular member or annular member is attached in the vicinity of the insertion hole 9 of said fixing member 5 as an exposure prevention member 10 for preventing the exposure of said angled needle 2.

(6) According to the present invention, further, there is provided a winged angled needle assembly as recited in (5), wherein the exposure prevention member 10 formed of said tubular member or annular member is attached to an outer circumference of said insertion hole 9.

(7) According to the present invention, further, there is provided a winged angled needle assembly as recited in any one of (1) to (7), wherein an upper portion of said guard 6 is attached to said hub 3 and a lower portion of said guard 6 is attached to said fixing member 5.

(8) According to the present invention, further, there is provided a winged angled needle assembly as recited in any one of (1) to (7), wherein said angled needle is made of a metal.

(9) According to the present invention, further, there is provided a winged angled needle assembly as recited in any one of (1) to (8), wherein said fixing member 5 has the form of a plate having a form selected from the group consisting of a rectangle, a circle and an ellipse.

(10) According to the present invention, further, there is provided a winged angled needle assembly as recited in (9), wherein said fixing member 5 is formed from a hard material selected from the group consisting of a hard plastic and a hard paper.

(11) According to the present invention, further, there is provided a winged angled needle assembly as recited in any one of (1) to (10), wherein said guard 6 is formed in the form of bellows.

(12) According to the present invention, further, there is provided a winged angled needle assembly as recited in (11), wherein said guard 6 is formed from a material having excellent hinging performances, which material is selected from the group consisting of polyethylene and polypropylene.

BRIEF DESCRIPTION OF DRAWINGS

FIG. 1 is a schematic drawing of one embodiment of the winged angled needle assembly of the present invention, in which

FIG. 2 is a schematic drawing of one embodiment of the winged angled needle assembly of the present invention, in which

FIG. 3 is a schematic drawing of one embodiment of the winged angled needle assembly of the present invention, in which

FIG. 4 is a schematic drawing of one embodiment of the winged angled needle assembly of the present invention, in which

FIG. 5 is a schematic drawing of one embodiment of the winged angled needle assembly of the present invention, in which

FIG. 6 is a schematic drawing of one embodiment of the winged angled needle assembly of the present invention, in which

FIG. 7 is a schematic drawing of one embodiment of the winged angled needle assembly of the present invention, in which

FIG. 8 is a schematic drawing of one embodiment of the winged angled needle assembly of the present invention, in which

FIG. 9 is a schematic drawing of one embodiment of the winged angled needle assembly of the present invention, in which

FIG. 11 is a schematic drawing of still another embodiment of the winged angled needle assembly of the present invention, in which

Figure 1A:
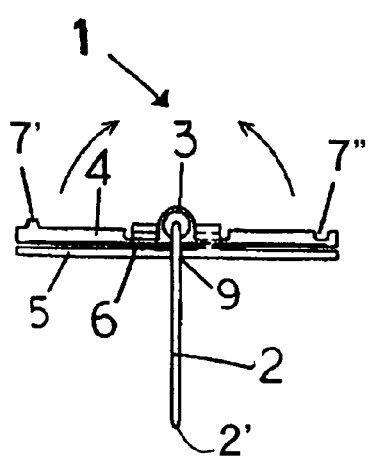
FIG. 1A is a front view.
Figure 1B:
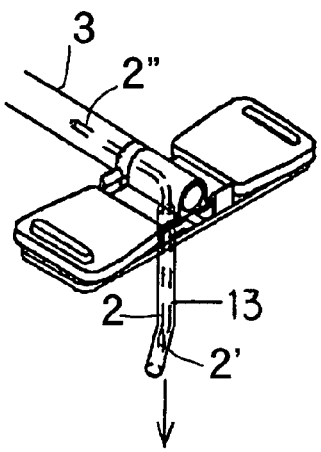
FIGS. 1B and 1C are perspective views.

In the drawings, reference numeral 1 indicates a winged angled needle assembly, numeral 2 indicates an angled needle, numeral 2' indicates a tip portion, numeral 2" indicates a proximal end portion, numeral 3 indicates a hub, numeral 4 indicates a wing, numeral 5 indicates a fixing member, numeral 6 indicates an extendable, contractible needle guard, numeral 7 indicates an engagement portion constituted of a projection 7' and a groove 7', numeral 8 indicates a stop member, numeral 9 indicates an insertion hole, numeral 10 indicates an exposure prevention portion formed of a tubular or annular member for preventing the exposure of an angled needle, and numerals 11 and 12 indicate engagement members. For example, when the engagement member 11 is a concave portion (or a groove), the engagement member 12 is a convex portion (or a projection). Numeral 13 indicates a tubular cover for an angled needle, and numeral 13T indicates a T-letter-shaped cover.

DESCRIPTION OF THE PREFERRED EMBODIMENT

The present invention will be explained below with reference to drawings. FIGS. 1 to 9 show a preferred embodiment of the winged angled needle assembly of the present invention.

(Basic Constitution of Winged Angled Needle Assembly of the Present Invention)

As shown in the drawings, the winged angled needle assembly or device 1 of the present invention has a hub (or support) 3 to which the proximal end portion 2' of an angled needle 2 having a sharpened tip portion 2' is joined and a pair of wings 4 attached to both side potions of the hub 3.

As shown, for example, in FIG. 1A, the above winged angled needle assembly 1 has a fixing member 5 attached so as to support the above wings 4 and an extendable and contractible needle guard or needle protective shield 6 disposed between the above hub 3 and the above fixing member 5 so as to connect these two members, the hub 3 and fixing member 5.

FIGS. 5 to 9 show the process of pulling the angled needle 2 out of an implanted port after the infusion of a therapeutic fluid or the like. In this process, the above guard 6, that is being folded when the needle is in use, is extended. In the extension procedure, the guard is extended in the direction from the above proximal end portion 2" of the angled needle 2 toward the above tip portion 2', so that the guard 6 can encase the tip portion 2' therein.

(Wings)

Figure 2A:
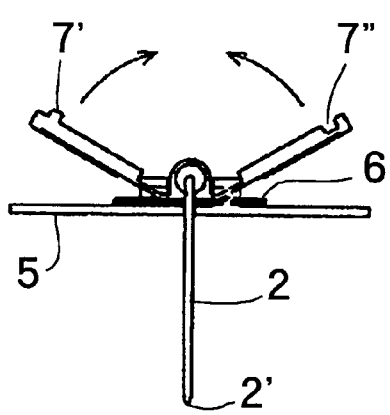
FIG. 2A is a front view.
Figure 2B:
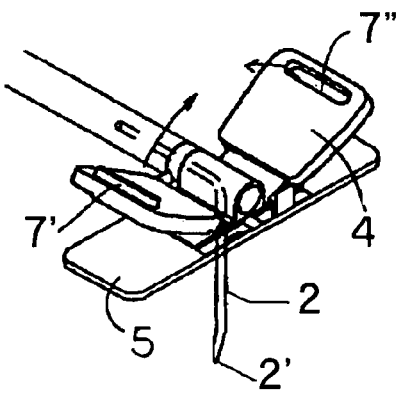
FIG. 2B is a perspective view.
Figure 3A:
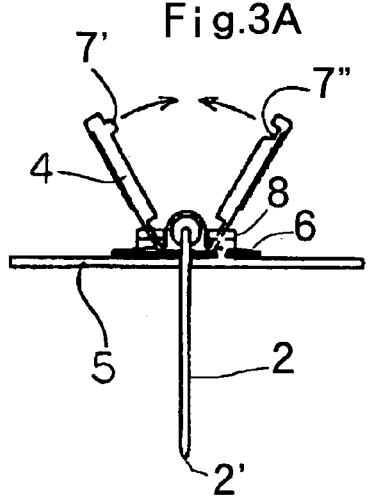
FIG. 3A is a front view and FIG. 3B is a perspective view.
Figure 3B:
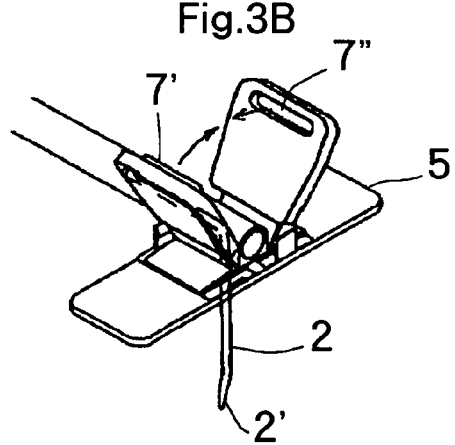
Figure 4A:
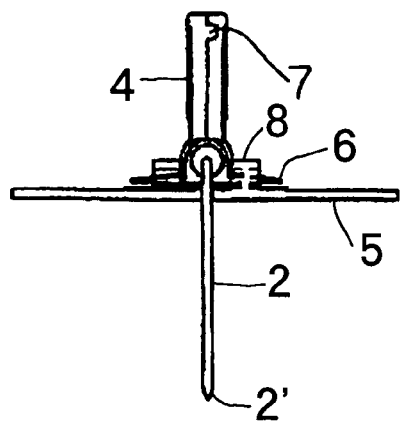
FIG. 4A is a front view and FIG. 4B is a perspective view.
Figure 4B:
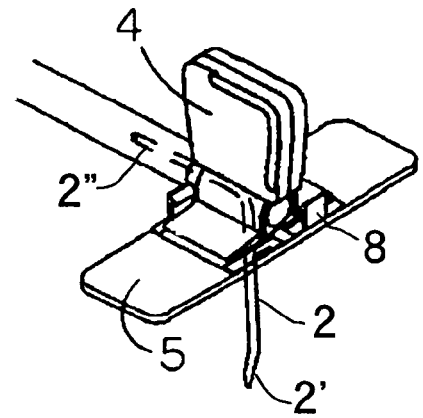

The wings are in principle similar to those of any conventional winged angled needle assembly, and a pair of the wings is attached to the two sides of the hub. The wings are constituted to be openable and closable. When the angled needle is used, the wings are opened to be coplanar with each other as shown in FIG. 1, and when the angled needle is pulled out of a port, they can be folded and closed to be placed on each other as shown in FIGS. 2 to 4. To ensure a reliable fixing of the wings, particularly in the closed state, engagement portions 7, consisting of a projection 7' and a groove 7" that are engageable with each other, are formed on upper or end portions of the above two wings 4. When the two wings are pulled upward to be placed on each other, the projection and groove engage with each other, thereby the wings can be firmly fixed. The term "engagement" means generally the state wherein the projection intrudes itself into the groove and the two members become joined with each other thereby the wings are fixed. And this term is used in a broad sense that includes a case wherein the projection and the groove are tightly coupled or joined (tight engagement) and a case wherein they come into light contact (stopping or fitting).

Further, the wings 4 are preferably formed to have thinner portions of smaller thickness, adjacent to the hub 3, so that the wings 4 can be easily pulled upward when closing the wings. Concerning the form of the wings 4, FIGS. 1 to 9 illustrate the wings having a rectangular form each. However, the form of the wings 4 shall not be specifically limited, and they may have the form of a semi-circle, a semi-ellipse, or the like.

The material for constituting the wings can be selected from those that are used for constituting conventional wings. Examples of the material preferably used include semi-hard or hard resins such as polyethylene, polypropylene, polyvinyl chloride, polycarbonate, polymethyl methacrylate, polyurethane, polyamide, polystyrene, polyethylene terephthalate, polyphenylene sulfide, polyether ether ketone, polyacetal, and the like.

(Fixing Member)

The winged angled needle assembly 1 of the present invention has a fixing member 5 so attached to support the wings 4 as shown, for example, in FIG. 1A. The fixing member 5 is a member that supports the wings opened to be coplanar with each other as shown in FIG. 1A and that is a necessary part for securing stable fixing of the winged angled needle assembly 1 to the implanted port in an installed state. Further, it is also a part that works as a support for pulling the angled needle 2 out of the port as shown in FIGS. 2 to 9. Having the above fixing member 5, the winged angled needle assembly 1 of the present invention is considerably improved in operability.

Although FIGS. 1 to 9 show the fixing member 5 having the form of a rectangular plate, the fixing member 5 may be a plate having a form of a rectangle, a circle, an ellipse, or the like when viewed as a plan view. Further, the material for constituting the fixing member 5 can be selected, in principle, from those materials described as examples of the material for the wings. Examples of the material used preferably include semi-hard or hard resins such as polyethylene, polypropylene, polyvinyl chloride, polycarbonate, polymethyl methacrylate, polyurethane, polyamide, polystyrene, polyethylene terephthalate, polyphenylene sulfide, polyether ether ketone, polyacetal, and the like. Further, the fixing member 5 may be formed from a hard paper material such as a corrugated fiberboard, or the like.

In the center of the above fixing member 5, there is formed an insertion hole (or a hole) 9 through which the angled needle 2 is inserted. The fixing member 5 is attached to the angled needle 2 by inserting the angled needle 2 through the insertion hole of the fixing member 5. Further, when the inserted angled needle 2 is pulled out, the angled needle 2 can be pulled out in a manner in which the proximal end portion 2" first passes through the insertion hole and then the sharpened tip portion 2' passes through said insertion hole.

Preferably, in the vicinity of the above insertion hole 9, there is provided an exposure prevention member 10 for preventing the exposure of the angled needle 2. Specifically, a tubular or annular member is attached to (or arranged around) the circumferential surface of the insertion hole 9, in a protruding manner, thereby the exposure of the sharpened tip portion 2' of the angled needle 2 from the guard 6 through the insertion hole (hole) 9 can be prevented, after the angled needle 2 is once encased in the guard 6.

(Guard)

The winged angled needle assembly 1 of the present invention has an extensible (expandable) and contractible (foldable) needle guard 6 that is disposed between the above hub 3 and the above fixing member 5 so as to connect these two members.

Figure 6A:
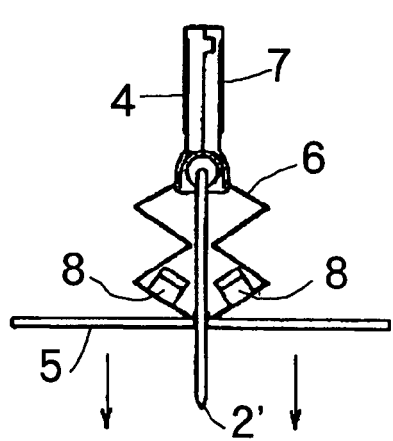
FIG. 6A is a front view and FIG. 6B is a perspective view.
Figure 6B:
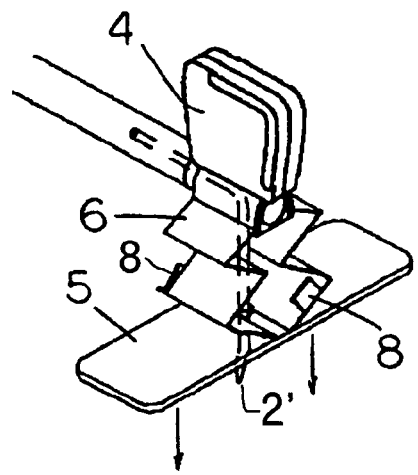
Figure 7A:
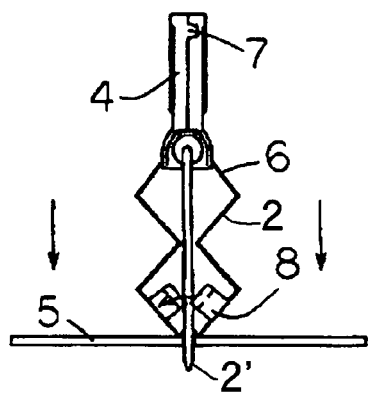
FIG. 7A is a front view and FIG. 7B is a perspective view.
Figure 7B:
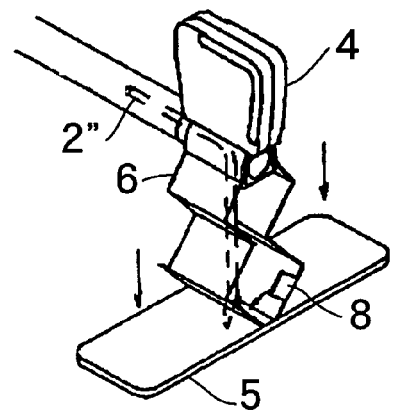
Figure 8A:
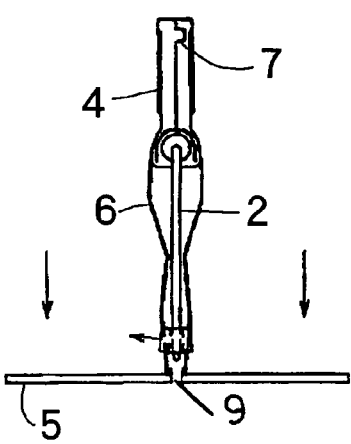
FIG. 8A is a front view and FIG. 8B is a perspective view.
Figure 8B:
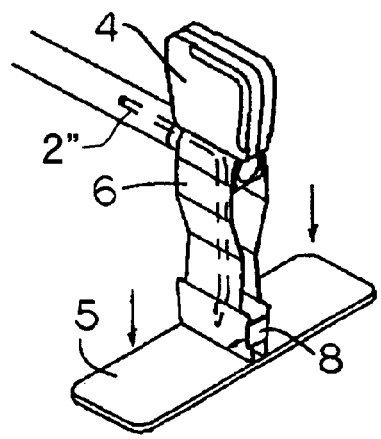
Figure 9A:
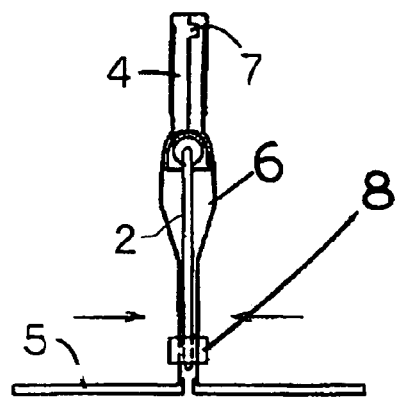
FIG. 9A is a front view and FIG. 9B is a perspective view.
Figure 9B:
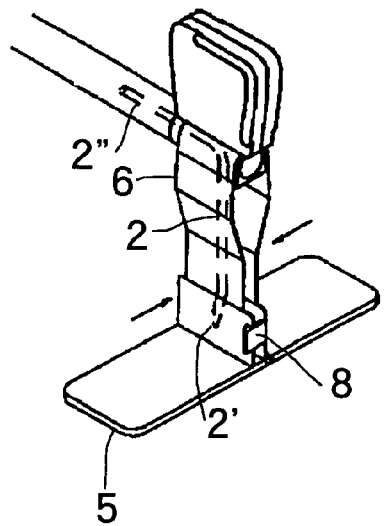
Figure 10A:
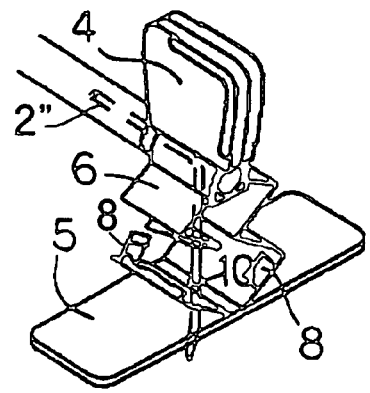
FIG. 10 is a schematic drawing of another embodiment of the winged angled needle assembly of the present invention.
Figure 11A:
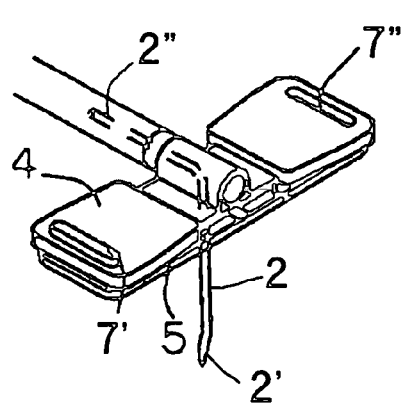
FIG. 11A is a perspective view of a state corresponding to the position in FIG. 1.
Figure 11B:
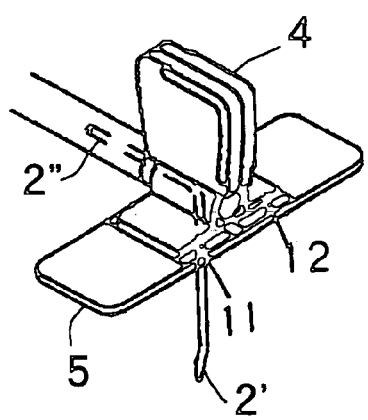
FIG. 11B is a perspective view of a state corresponding to the position in FIG. 4.
Figure 11C:
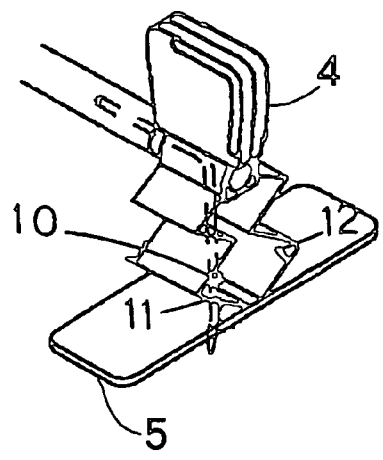
FIG. 11C is a perspective view of a state corresponding to the position in FIG. 6.
Figure 11D:
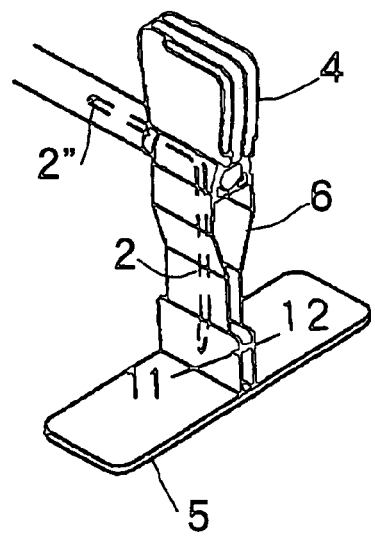
FIG. 11D is a perspective view of a state corresponding to the position in FIG. 9.

FIGS. 5 to 9 show the process of pulling the angled needle 2 out of an implanted port after completion of the infusion of a therapeutic fluid or the like. In this procedure, the guard 6 that has been contracted or folded as shown in FIGS. 1 to 4, is extended as the angled needle 2 is pulled out. During the extension, the guard 6 extends or expands from the proximal end portion 2" of the angled needle 2 toward the above sharpened tip portion 2', so that the tip portion 2' can be finally encased in the above guard 6 as shown in FIGS. 8 and 9. The guard 6 is required not only to contract or collapse but also to extend or expands described above, so that the guard 6 is, formed preferably, in the form of bellows, which is easily contractible (collapsible) and extensible (expandable) with ease.

Further, the guard 6 preferably has, attached thereto, an exposure prevention means for preventing the exposure of the angled needle as shown in FIGS. 1 to 9. The exposure prevention means includes stop members 8 such as a stop plate, a stop bar, a stop hook, or the like, and engagement members 11 and 12, and these means are attached to the guard 6. The stop members 8 are attached to both sides (underside surfaces) of the guard 6 so as to be opposed to each other as shown in FIGS. 1 to 9. The engagement members 11 and 12 are formed in the form of a concave portion (or groove) 11 and a convex portion (or projection) 12 which are attached to both sides (underside surfaces) of the guard 6 so as to be opposed to each other as shown in FIG. 11. The term "engagement" means the state wherein the convex portion (or projection) intrudes itself into the concave portion (groove), and the two members become joined with each other, thereby the guard is firmly fixed. And this term is used in a broad sense that includes a case wherein the convex portion (projection) and the concave portion (groove) are tightly coupled (tight engagement) and a case wherein they come into light contact (stopping or fitting).

The material for constituting the guard 6 can be selected, in principle, from those materials described for the wings and fixing members. Examples of the material include preferably semi-hard or hard resins such as polyethylene, polypropylene, polyvinyl chloride, polycarbonate, polymethyl methacrylate, polyurethane, polyamide, polystyrene, polyethylene terephthalate, polyphenylene sulfide, polyether ether ketone, polyacetal, and the like. Preferably, the guard 6 is formed, particularly, in the form of bellows, which is easily collapsible and extendable. For this purpose, the guard 6 is preferably formed, particularly, from a material having excellent hinging performances, such as polypropylene, polyethylene, or the like.

The guard 6 is disposed between the hub 3 and the fixing member 5 and connects these two members. Specifically, there may be employed a constitution for connection, in which suitable corresponding fitting structures are formed in the upper and lower portions of the guard, the hub and the fixing member, and the corresponding structures are mechanically fitted to, or caused to join, each other to connect the corresponding members by engagement, stopping, binding, or the like. Further, the above guard, hub and fixing member may be integrally formed to constitute joined structures. Further, they may be connected by solvent bonding, adhesive bonding, or the like, or they may be connected by weld bonding by applying heat, high-frequency waves, or the like.

(Positional Relationship of Angled Needle, Wings and Guard)

The angled needle 2, the wings 4 and the guard 6 have the following mutual relationships in positions before and after the use of the winged angled needle assembly.

With regard to the position of these members before use of the winged angled needle assembly (protective position before use, i.e., a position before the angled needle pierces an implanted port) and the position during the use thereof (installed position, i.e., a position in a state wherein the angled needle 2 pierces the port), the guard is contracted (collapsed), and the angled needle 2 is exposed, as shown in FIGS. 1 to 4. In the protective position before use, the winged angled needle assembly has a tubular cover 13 or a T-letter-shaped cover 13T attached to the angled needle 2 for protecting the exposed angled needle 2, as shown in FIG. 1B or FIG. 1C.

In the protective position after use of the winged angled needle assembly (that is, a position in which the angled needle 2 is pulled out of the port and discarded after infusion of therapeutic fluid or the like), the angled needle 2 is encased in the guard 6 that extends from the proximal end portion 2" of the angled needle 2 to the sharpened tip portion 2' thereof in parallel with the angled needle 2, as shown in FIG. 9.

Meanwhile, in the protective position before use of the winged angled needle assembly and the installed position during the use thereof (a position in a state where the angled needle 2 pierces the implanted port and therapeutic fluid, or the like is administered), the wings 4 are in an opened state and positioned perpendicular to the angled needle 2 as shown in FIG. 1. In the installed position and the protective position after use, the wings are in a closed state and positioned in parallel with the angled needle 2 as shown in FIGS. 4 to 9.

(Method of Use)

The winged angled needle assembly 1 of the present invention will be explained below with regard to one embodiment of the method of use or operation thereof with reference to the drawings.

Figure 1C:
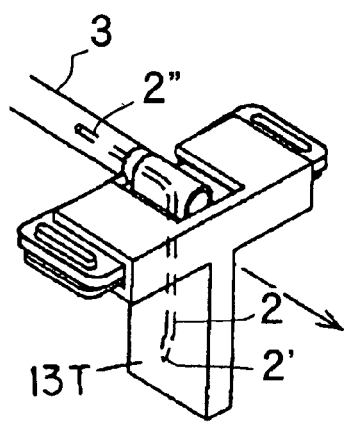

(1) In the state before use as shown, the angled needle 2 has, attached thereto, a tubular cover 13 (see FIG. 1B) or a T-letter-shaped cover 13T (see FIG. 1C). The cover attached to the angled needle 2 is then removed. In this state, as is shown in FIG. 1A, the wings 4 are in an open state to be coplanar to each other and are positioned on the fixing member 5, and the guard 6 is positioned between the wings 4 and fixing member 5, in the state of being folded (collapsed) between the wings 4.

(2) As shown in FIG. 2, the end portions of the wings 4 are grabbed and lifted (pulled) upward to close the wings 4. The wings 4 are firmly fixed in a closed state by mutual tight engagement of the projection 7' and the groove 7", constituting the engagement portion 7.

(3) In the state shown in FIG. 4, the angled needle 2 is caused to pierce an implanted port (implanted in the body of a patient (not shown)), and in the state shown in FIG. 1, the fixing member 5 is fixed to the patient's skin above the implanted port with an adhesive tape, or the like. Like the fixing member 5, further, the wings 4 are also fixed in parallel with the skin of the patient with an adhesive tape, thereby the winged angled needle assembly 1 is fixed and does not move during the administration of therapeutic fluid or the like.

Figure 5A:
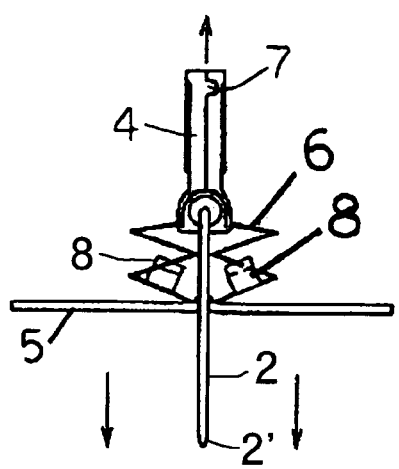
FIG. 5A is a front view and FIG. 5B is a perspective view.
Figure 5B:
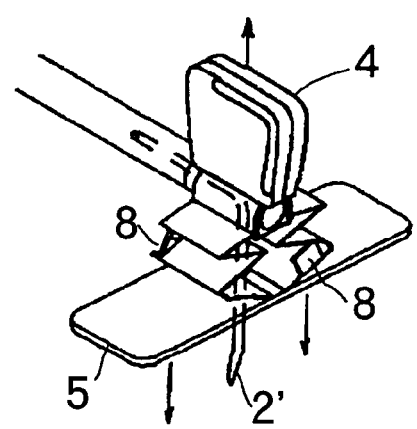

(4) After completion of the infusion of the therapeutic fluid or the like, the left and right wings 4 are folded back as shown in FIGS. 2 to 4, and the wings 4 are lifted (pulled) upward as shown in FIGS. 5 to 7, so that the guard 6 extends in parallel with the direction from the proximal end portion 2" of the angled needle 2 to the sharpened tip portion 2' thereof, and thereby encases the sharpened tip of the angled needle 2 in the guard 6 as shown in FIGS. 8 and 9.

In this case, the guard has, attached thereto, exposure prevention means such as stop members 8 constituted of two stop plates, stop hooks, or the like or engagement members 11 and 12 constituted of a concave portion (groove) and a convex portion (projection), and the fixing member 5 has a tubular member or annular member attached to the circumference of the insertion hole 9 as an exposure prevention member 10, so that when the sharpened tip 2' of the angled needle 2 is encased in the guard 6, the guard 6 is externally stopped at the same time. Therefore, it is completely secured that the sharpened tip 2' of the angled needle 2 never comes out of the guard and exposed in any case.

(Function and Effect of the Invention)

The winged angled needle assembly of the present invention has the following functions and advantageous effects.

(1) Since the winged angled needle assembly of the present invention has the fixing member 5 attached thereto, capable of supporting the wings, thereby allowing a free and flexible selection of an angled needle having any desired or required length, regardless of the length of the wings. The broader therapeutic applications of the winged angled needle assembly can be made.

(2) When an angled needle is pulled out of an implanted port, the winged angled needle assembly of the present invention, having been provided for the fixing member 5, can secure a sufficient support (scaffold), so that the angled needle can be easily pulled out, even if it is caused to be pushed into and pierce the implanted port tightly. Therefore, the winged angled needle assembly is excellent in operability and minimizes the mental stress of a patient.

(3) In the winged angled needle assembly of the present invention, the sharpened tip portion of the angled needle is encased in the guard 6, simultaneously with pulling the angled needle out of an implanted port. Further, the guard 6 has the exposure prevention means attached thereto and the guard 6 is externally stopped, so that the sharpened tip of the angled needle 2, never comes out of the guard and exposed, once it is encased in the guard. Therefore, the accidental needle sticking of medical practitioners can be assuredly prevented.

(4) In the winged angled needle assembly of the present invention, the angled needle that is to pierce an implanted port, is made of a metal, the rigid material, so that there is completely no danger of kinking that may take place with a conventional cannula formed of a tube of PTFE or the like, and also no danger of plugging of flow that may be caused by the repulsive force of an implanted port formed of an elastomeric material such as silicone, or the like.

What is claimed is:

1. A winged angled needle assembly comprising a hub to which a proximal end portion of an angled needle having a sharpened tip portion is joined and a pair of wings attached to both sides of said hub, said wings are configured to be openable and closable, being open to be coplanar with each other when the needle is in use, and after use, being folded on each other when a stained needle is being pulled out and discarded, the winged angled needle assembly further comprising a fixing member attached so as to support said wings when said wings are opened, and an extendable, contractible needle guard disposed between said hub and said fixing member so as to connect these two members, wherein said needle guard is composed of two opposing hinged plates, configured to extend and encase the whole part of the angled needle with its sharpened tip portion between the opposing hinged plates when extended, wherein said opposing hinged plates have attached thereto, stop members or engagement members configured to prevent the exposure of the encased angled needle, said members are disposed to be opposed with each other, thereby securing the encased angled needle between the opposing hinged plates, thereby said needle guard being folded when the needle is in use, and after use extends in the direction from said proximal end portion of said stained needle to said sharpened tip portion when extended, so that all of said stained needle to be discarded, including the stained tip portion can be encased and secured in said guard when the stained needle is discarded.

2. The winged angled needle assembly as recited in claim 1, wherein said fixing member has an insertion hole between the opposing hinged plates through which said angled needle is to be inserted, the insertion hole being formed nearly in the center of said fixing member, the winged angled needle assembly having a constitution in which the angled needle can be inserted through said insertion hole when said winged angled needle assembly is used, and said angled needle can be pulled out in a manner in which the proximal end portion first passes through the insertion hole and then the sharpened tip portion passes through the insertion hole.

3. The winged angled needle assembly as recited in claim 1, wherein (i) a stop plate or stop hook is attached as said stop members to said guard composed of opposing hinged plates, so as to be opposed with each other and (ii) a concave portion or groove and a convex portion or projection are attached as said engagement members to said guard composed of opposing hinged plates, so as to be opposed with each other.

4. The winged angled needle assembly as recited in claim 1, wherein a tubular member or annular member is attached in the vicinity of the insertion hole of said fixing member as an exposure prevention member for preventing the exposure of said angled needle.

5. The winged angled needle assembly as recited in claim 4, wherein the exposure prevention member formed of said tubular member or annular member is attached to an outer circumference of said insertion hole.

6. The winged angled needle assembly as recited in claim 1, wherein an upper portion of said guard is attached to said hub and a lower portion of said guard is attached to said fixing member.

7. The winged angled needle assembly as recited in claim 1, wherein said angled needle is made of a metal.

8. The winged angled needle assembly as recited in claim 1, wherein said fixing member has the form of a plate having a form selected from the group consisting of a rectangle, a circle and an ellipse.

9. The winged angled needle assembly as recited in claim 8, wherein said fixing member is formed from a hard material selected from the group consisting of a hard plastic and a hard paper.

10. The winged angled needle assembly as recited in claim 1, wherein said guard is formed in the form of bellows.

11. The winged angled needle assembly as recited in claim 1, wherein said guard is formed from a material having excellent hinging performances, which material is selected from the group consisting of polyethylene and polypropylene.

* * * * *